US00PP28937P3

(12) United States Plant Patent
Ranney

(10) Patent No.: US PP28,937 P3
(45) Date of Patent: Feb. 6, 2018

(54) ***ILEX* PLANT NAMED 'NCIV3'**

(50) Latin Name: *Ilex verticillata*
Varietal Denomination: NCIV3

(71) Applicant: North Carolina State University, Raleigh, NC (US)

(72) Inventor: Thomas Green Ranney, Arden, NC (US)

(73) Assignee: North Carolina State University, Raleight, NC (US)

( * ) Notice: Subject to any disclaimer, the term of this patent is extended or adjusted under 35 U.S.C. 154(b) by 0 days.

(21) Appl. No.: 14/999,194

(22) Filed: Apr. 7, 2016

(65) Prior Publication Data

US 2017/0295686 P1 Oct. 12, 2017

(51) Int. Cl.
*A01H 5/12* (2006.01)

(52) U.S. Cl.
USPC ..... Plt./247

(58) Field of Classification Search
USPC ..... Plt./247
See application file for complete search history.

*Primary Examiner* — Keith O Robinson
(74) *Attorney, Agent, or Firm* — Cassandra Bright

(57) ABSTRACT

'NCIV3' is a new male tetraploid cultivar of deciduous holly with a compact, roughly rounded growth habit.

1 Drawing Sheet

Latin name of the genus and species: The Latin name of the novel plant variety disclosed herein is *Ilex verticillata.*

Variety denomination: The inventive seedling selection of *Ilex verticillata* disclosed herein has been given the varietal denomination 'NCIV3'.

BACKGROUND OF THE INVENTION

The present invention comprises a new and distinct male winterberry holly cultivar hereinafter referred to by the cultivar name 'NCIV3'. This new holly was developed at North Carolina State University, Mills River, N.C. 'NCIV3' was selected from a population of seedlings grown from an open-pollinated selection of *Ilex verticillata* (NCSU 1998-538, unpatented, parentage unknown). 'NCIV3' was selected based on its compact form. DNA content of 'NCIV3' was determined using flow cytometry and found to be approximately twice that of *I. verticillata* 'Southern Gentleman' indicating that 'NCIV3' is a natural tetraploid.

The first asexual propagation of 'NCIV3' was carried out in July 2008 by rooting stem cuttings at the North Carolina State University, Mountain Horticultural Crops Research Station, Mills River, N.C. and has been asexually reproduced repeatedly by vegetative cuttings over a 9 year period. 'NCIV3' roots readily from softwood cuttings treated with a basal dip of 2,500-5,000 ppm indole butyric acid (potassium salt) in water. 'NCIV3' has been found to retain its distinctive characteristics through successive asexual propagations.

SUMMARY OF THE INVENTION

The following are the unique combination of characteristics of this new cultivar when grown under standard horticultural practices at North Carolina State University, Mountain Horticultural Crops Research Station, Mills River, N.C.

1. Compact habit and small stature.
2. Male selection (dioecious).

3. 2C DNA content of approximately 4.27 pg indicating it is a tetraploid cytotype.

BRIEF DESCRIPTION OF THE DRAWINGS

This new holly is illustrated by the accompanying photograph which show the plant's form. The colors shown are as true as can be reasonably obtained by conventional photographic procedures. Colors in the photographs may differ slightly from the color values cited in the detailed botanical description, which accurately describe the colors of the new hybrid holly.

FIG. 1 is a color photograph showing the form 'NCIV3' in early spring 2014 on a nine-year-old plant in Mills River, N.C.

DETAILED BOTANICAL DESCRIPTION

The following is a detailed description of the botanical characteristics of the new and distinct holly variety known by the denomination 'NCIV3'. The detailed description was taken on a nine-year-old field-grown plant in Mills River, N.C. in 2014. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety

Classification:

*Botanical name.*—*Ilex verticillata* 'NCIV3'.

*Common name.*—Winterberry holly.

Parentage: Seedling grown from an open-pollinated selection of *Ilex verticillata*, NCSU 1998-538 (unpatented).

Plant description:

*Growth habit.*—Deciduous shrub. Compact, rounded/oval in shape.

*Height.*—About 78 cm after nine years.

*Width.*—About 82 cm after nine years.

Shoot and stem:

*Mature stem texture.*—Finely pubescent, with lenticels.

*Mature stem color.*—Brown (197B) with brown (N200D) lenticels.

Lateral branches:

*Length.*—About 15 cm.

*Diameter.*—About 4 mm.

*Internode length.*—About 3.5 cm.

*Strength.*—Strong.

*Texture.*—Smooth, glabrous.

*Color.*—Immature: Green (138A). Mature: Grayed-green (198A).

*Lenticels.*—Length: About 1 mm. Diameter: About 1 mm. Color: Grey-brown (199C) to grey-brown (199D).

Roots: Fibrous, freely branching.

Leaves:

*Arrangement.*—Alternate, single.

*Length.*—Avg. 4.5 cm (1.5 to 7.5 cm).

*Width.*—Avg. 2.25 cm (1.1 to 3.4 cm).

*Shape.*—Elliptic.

*Apex.*—Apiculate.

*Base.*—Attenuate.

*Margin.*—Serrulate.

*Venation pattern.*—Pinnate.

*Texture.*—Upper Surface: Smooth, glabrous. Lower Surface: Pubescent, slightly rugose.

*Fragrance.*—None.

*Aspect.*—Flat.

*Quantity per lateral branch.*—75 to 150.

*Emerging leaves.*—Color: Upper: Yellow-Green (144A). Lower: Yellow-green (144A).

*Mature leaves during growing season.*—Color: Upper: Green (139A). Lower: Green (147B).

*Venation.*—Upper Surface: Green (137A). Lower Surface: Yellow-green (145C).

*Petiole.*—Length: Avg. 9 mm (5 to 13 mm). Diameter: Avg. 0.67 mm (0.4 to 0.94 mm). Texture: Upper: Glabrous. Lower: Glabrous. Color: Upper: Yellow-green (145C). Lower: Yellow-green (145C).

*Leaf bud.*—Length: 1 mm. Diameter: 1 mm. Texture: Slightly rough.

*Stipules.*—Not present.

Inflorescence:

*Description.*—Small axillary cup shaped flowers, solitary. Flowers face upright to outward. Flowers not persistent.

*Number of true flowers per inflorescence.*—1.

*Flowering season.*—Summer; June and July in Mills River, N.C.

*Fragrance.*—None detected.

*Bud.*—Shape: Globular. Length: About 2 mm. Diameter: About 2 mm. Color: Green-white (157A).

*Flower.*—Diameter: 1 mm. Length: 1 mm.

*Petal.*—Arrangement: Whorl. Number: 7. Fused: Not fused. Texture: Smooth. Shape: Oblong. Margin: Entire. Apex: Rounded. Base: Attenuate. Length: About 4 mm. Width: About 2 mm. Texture: Upper: Smooth, glabrous. Lower: Smooth, glabrous. Color when opening: Upper: White (157B). Lower: White (157A). Color at anthesis: Upper: Green-white (157B). Lower: Green-white (157A).

*Sepal.*—Quantity per flower: 7. Length: About 2.5 mm. Width: About 2 mm. Shape: Deltoid. Apex: Acute. Base: Fused. Margin: Entire. Texture: Upper: Smooth, glabrous. Lower: Smooth, glabrous. Color: Upper: Yellow-green (144A). Lower: Yellow-green (144A).

*Peduncle.*—Length: About 2 mm. Diameter: About 1 mm. Orientation: About 20 to 40 degrees from vertical. Strength: Strong. Color: Yellow-green (144A).

Reproductive traits:

*Sex.*—Functional male (dioecious).

*Gynoecium.*—None.

*Androcoecium.*—Stamen number: 7. Anther shape: Narrowly deltoid. Anther attachment: Basifixed. Anther size: About 1 mm long and less than 0.5 mm wide. Anther color: Green-white (157D). Amount of pollen: Abundant. Pollen color: Near RHS Yellow 9A.

*Fruit and seed.*—Male selection. No fruit or seed present.

DNA content: 2C DNA contend was determined following the methods of Shearer and Ranney (2013) using 4',6-diamidino-2-phenylindole (DAPI) fluorochrome stain and *Pisum sativum* 'Ctirad' (unpatented) as an internal standard with 3 replications. Mean 2C DNA content for 'NCIV3' was 4.27±0.07 (SEM) pg, approximately twice the value of *I. verticillata* 'Southern Gentleman' with a DNA content of 1.93±0.05 (SEM) pg indicating that 'NCIV3' is a tetraploid.

Disease and insect resistance: No significant disease or insect pests have been observed.

Cold hardiness: At least USDA zone 5; testing has not been completed in colder zones.

COMPARISON WITH COMMERCIAL CULTIVARS

Table 1 shows comparison of distinguishing characteristics between *Ilex verticillata* 'NCIV3', the female parent (NCSU 1998-538), and the commercial cultivar 'Southern Gentleman'. 'NCIV3' is distinguished from *Ilex verticillata* 'Southern Gentleman' by having twice the genomic DNA content indicating it is a tetraploid and having a smaller, more compact stature.

TABLE 1

Comparison of *Ilex verticillata* taxa

| Trait | *Ilex verticillata* 'Southern Gentleman' | *Ilex verticillata* NCSU 1998-538 | *Ilex verticillata* 'NCIV3' |
|---|---|---|---|
| Plant height & diameter | About 96 in. × 96 in. | About 50 in. × 50 in. | About 31 in. × 33 in. |
| Plant habit | Erect, rounded shape | Rounded | Compact, roughly rounded shape |
| DNA content (pg) mean ± SEM | 1.93 ± 0.05 | 4.33 ± 0.05 | 4.27 ± 0.07 |
| Estimated ploidy level | Diploid | Tetraploid | Tetraploid |
| Sex | Male | Female | Male |

What is claimed is:

1. A new and distinct hybrid holly plant named 'NCIV3' substantially as illustrated and described herein.

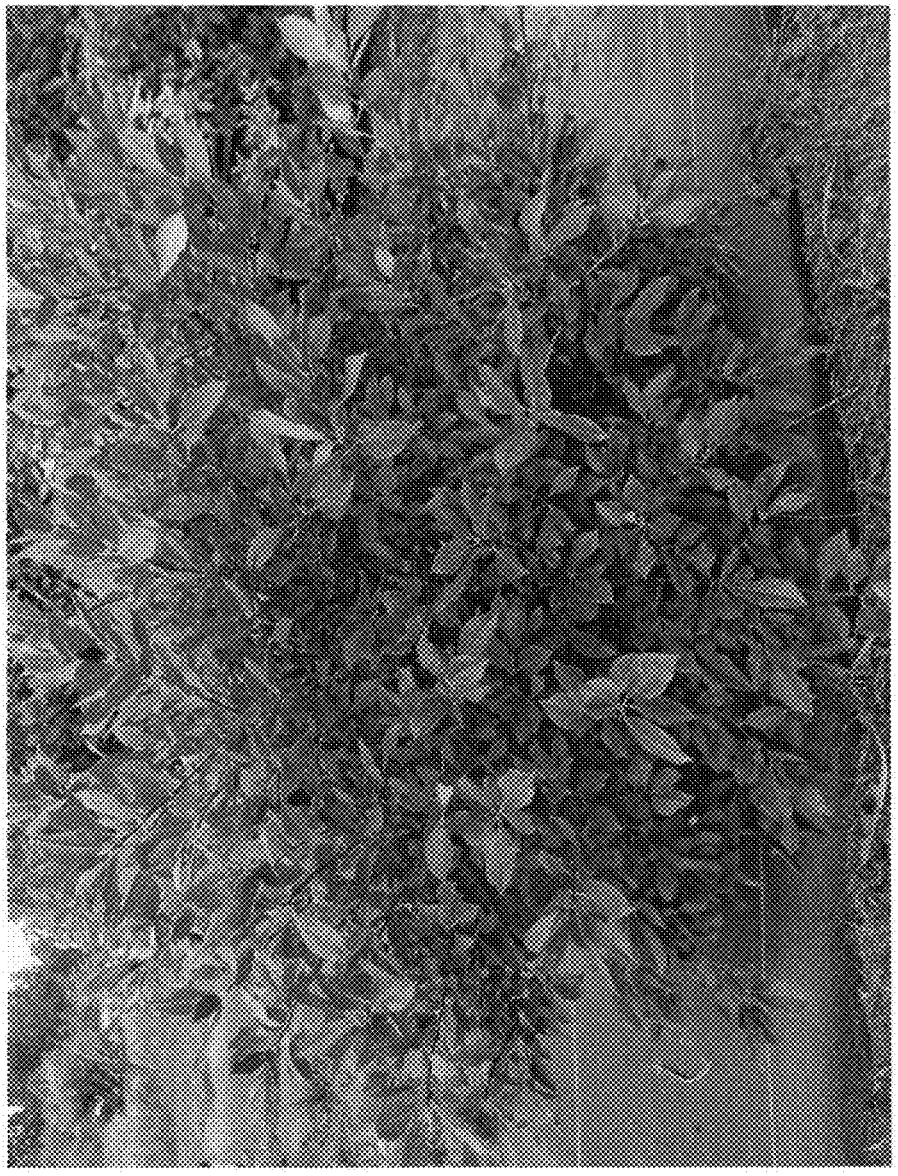

* * * * *